(12) United States Patent
Cancedda et al.

(10) Patent No.: US 9,822,368 B2
(45) Date of Patent: Nov. 21, 2017

(54) MODULATORS OF INTRACELLULAR CHLORIDE CONCENTRATION FOR TREATING DOWN SYNDROME

(71) Applicants: Fondazione Istituto Italiano di Tecnologia, Genoa (IT); B & A Therapeutics, Maseilles (FR)

(72) Inventors: Laura Cancedda, Genoa (IT); Yehezkel Ben-Ari, La Ciotat (FR); Andrea Constestabile, Genoa (IT)

(73) Assignees: FONDAZIONE ISTITUTO ITALIANO DI TECNOLOGIA, Genoa (IT); B&A THERAPEUTICS, Marseilles (FR)

( * ) Notice: Subject to any disclaimer, the term of this patent is extended or adjusted under 35 U.S.C. 154(b) by 22 days.

(21) Appl. No.: 15/104,895

(22) PCT Filed: Dec. 18, 2014

(86) PCT No.: PCT/EP2014/078561
§ 371 (c)(1),
(2) Date: Jun. 15, 2016

(87) PCT Pub. No.: WO2015/091857
PCT Pub. Date: Jun. 25, 2015

(65) Prior Publication Data
US 2016/0312229 A1 Oct. 27, 2016

Related U.S. Application Data

(60) Provisional application No. 61/919,195, filed on Dec. 20, 2013.

(51) Int. Cl.
| | |
|---|---|
| *A61K 31/64* | (2006.01) |
| *C12N 15/113* | (2010.01) |
| *A61K 31/196* | (2006.01) |
| *A61K 31/40* | (2006.01) |
| *A61K 31/427* | (2006.01) |
| *A61K 31/517* | (2006.01) |
| *A61K 31/549* | (2006.01) |
| *A61K 31/635* | (2006.01) |
| *A61K 31/7105* | (2006.01) |

(52) U.S. Cl.
CPC ........ *C12N 15/1138* (2013.01); *A61K 31/196* (2013.01); *A61K 31/40* (2013.01); *A61K 31/427* (2013.01); *A61K 31/517* (2013.01); *A61K 31/549* (2013.01); *A61K 31/635* (2013.01); *A61K 31/64* (2013.01); *A61K 31/7105* (2013.01); *C12N 2310/11* (2013.01); *C12N 2310/12* (2013.01); *C12N 2310/122* (2013.01); *C12N 2310/14* (2013.01); *C12N 2310/16* (2013.01); *C12N 2310/531* (2013.01); *C12N 2320/32* (2013.01)

(58) Field of Classification Search
CPC ..................................................... A61K 31/64
See application file for complete search history.

(56) References Cited

U.S. PATENT DOCUMENTS

| | | |
|---|---|---|
| 3,985,777 A | 10/1976 | Feit |
| 4,247,550 A | 1/1981 | Feit et al. |
| 4,946,778 A | 8/1990 | Ladner et al. |
| 5,981,732 A | 11/1999 | Cowsert |
| 6,046,321 A | 4/2000 | Cowsert |
| 6,107,091 A | 8/2000 | Cowsert |
| 6,365,354 B1 | 4/2002 | Bennett et al. |
| 6,410,323 B1 | 6/2002 | Roberts et al. |
| 6,506,559 B1 | 1/2003 | Fire et al. |
| 6,566,131 B1 | 5/2003 | Cowsert |
| 6,566,135 B1 | 5/2003 | Watt |
| 6,573,099 B2 | 6/2003 | Graham |
| 7,282,519 B2 | 10/2007 | Garvey et al. |
| 2007/0155729 A1 | 7/2007 | Morgan et al. |

FOREIGN PATENT DOCUMENTS

| | | | |
|---|---|---|---|
| EP | 2298296 A1 | 3/2011 | |
| FR | EP 2298296 A1 * | 3/2011 | ........... A61K 9/0019 |
| GB | 2207129 A | 1/1989 | |
| WO | 99/32619 A1 | 7/1999 | |
| WO | 01/36646 A1 | 5/2001 | |
| WO | 01/68836 A2 | 9/2001 | |
| WO | 2006/110187 A3 | 10/2006 | |
| WO | 2011/024115 A1 | 3/2011 | |
| WO | 2011/086126 A1 | 7/2011 | |
| WO | 2012/018635 A3 | 2/2012 | |

OTHER PUBLICATIONS

PubChem. "Bumetanide." © 2017. Available from: < https://pubchem.ncbi.nlm.nih.gov/compound/bumetanide >.*
Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Verkman, A.S., et al. "Chloride channels as drug targets." Nat Rev. Drug Discov. (Feb. 2009): vol. 8, Issue 2, pp. 153-171, Available from: < https://www.ncbi.nlm.nih.gov/pmc/articles/PMC3601949/pdf/nihms448084.pdf >.*
Mayo Clinic. "Down syndrome." © 2017. Available from: < http://www.mayoclinic.org/diseases-conditions/down-syndrome/basics/prevention/con-20020948 >.*
Sigel, E., et al. "Structure, Function, and Modulation of GABAA Receptors." J. of Biological Chemistry. (Nov. 23, 2012), vol. 287, No. 48, pp. 40224-40231.*

(Continued)

*Primary Examiner* — Noble Jarrell
*Assistant Examiner* — John S Kenyon
(74) *Attorney, Agent, or Firm* — MacMillan, Sobanski & Todd, LLC

(57) ABSTRACT

Modulators of intracellular chloride concentration for treating down syndrome The present invention relates to a modulator of a chloride transporter for use in the treatment of Down syndrome.

6 Claims, 5 Drawing Sheets

(56) References Cited

OTHER PUBLICATIONS

Figure 1:
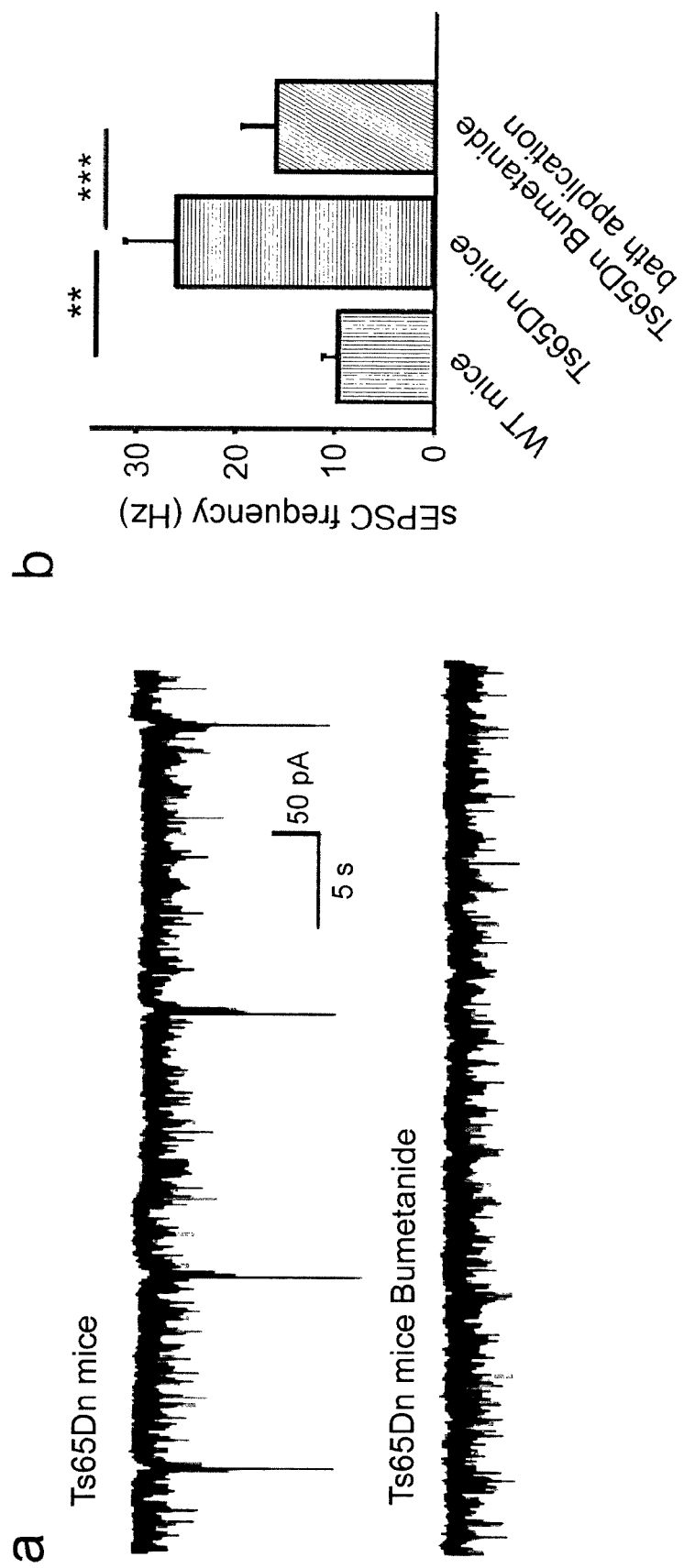

Brummelkamp et al., "A System for Stable Expression of Short Interfering RNAs in Mammalian Cells", Science, 2002, vol. 296, pp. 550-553.
Colas et al., "Genetic selection of peptide aptamers that recognize and inhibit cyclin-dependent kinase 2", Nature, 1996, vol. 380, pp. 548-550.
Cole et al., "Human monoclonal antibodies", Molecular and Cellular Biochemistry, 1984, vol. 62, pp. 109-120.
Cote et al., "Generation of human monoclonal antibodies reactive with cellular antigens", Proceedings of the National Academy of Science USA, 1983, vol. 80, pp. 2026-2030.
Elbashir et al., "Duplexes of 21-nucleotide RNAs mediate RNA interference in cultured mammalian cells", Nature, 2001, vol. 411, pp. 494-498.
Ettmayer et al., "Lessons Learned from Marketed and Investigational Prodrugs", Journal of Medicinal Chemistry, 2004, vol. 47, No. 10, pp. 2394-2404.
Gangon et al., "Characterization of SPAK and OSR1, Regulatory Kinases of the Na—K—2Cl Cotransporter", Molecular and Cellular Biology, 2006, vol. 26, No. 2, pp. 689-698.
Green et al., "Chapter 3: Cloning and Transformation with Plasmid Vectors", Molecular Cloning, A Laboratory Manual, Fourth Edition, pp. 157-161.
Hannon, "RNA interference", Nature, 2002, vol. 418, pp. 244-251.
Jayasena, "Aptamers: An Emerging Class of Molecules That Rival Antibodies in Diagnostics" Clinical Chemistry, 1999, vol. 45, No. 9, pp. 1628-1650.
Köhler et al., "Continuous cultures of fused cells secreting antibody of predefined specificity", Nature, 1975, vol. 256, pp. 495-497.
Kriegler, "Assembly of Enhancers, Promoters, and Splice Signals to Control Expression of Transferred Genes", Methods in Enzymology, 1990, vol. 185, pp. 512-527.
Lobaugh et al., "Piracetam Therapy Does Not Enhance Cognitive Functioning in Children With Down Syndrome" Archives of Pediatrics and Adolescent Medicine, 2001, vol. 155, pp. 442-448.
McManus et al., "Gene Silencing in Mammals by Small Interfering RNAs", Nature Reviews, 2002, vol. 3, pp. 737-747.
Reeves et al., "A mouse model for Down syndrome exhibits learning and behavior deficits", Nature Genetics, 1995, vol. 11, pp. 177-184.
Schacht et al., "Chapter 20: Poly(ethylene glycol)-Grafted Polymers as Drug Carriers", Poly(ethylene glycol) chemistry and Biological Applications, 1997, pp. 297-315.
Testa et al., "Chapter 1: Introduction: Metabolic Hydrolysis and Prodrug Design", Hydrolysis in Drug and Prodrug Metabolism, 2003, pp. 1-9.
Tuerk et al., "Systemic Evolution of Ligands by Exponential Enrichment: RNA Ligands to Bacteriophage T4 DNA Polymerase", 1990, Science, vol. 249, pp. 505-510.
Tuschl et al., "Targeted mRNA degradation by double-stranded RNA in vitro", Genes & Development, 1999, vol. 13, pp. 3191-3197.
Al-Zubalry et al., "Octreotide as a Therapeutic Option for Management of Chylothorax", Annals of Pharmacotherapy, 2003, vol. 37, pp. 679-682.
Arany et al., "Nanoparticle-mediated Gene Silencing Confers Radioprotection to Salivary Glands In Vivo", Molecular Therapy, 2013, vol. 21, No. 6, pp. 1182-1194.
Cobenas et al., "Another toddler with Down syndrome, nephrocalcinosis, hypercalcemia, and hypercalciuria", Pediatric Nephrology, 1998, vol. 12, No. 5, p. 432.
Cohen et al., "A 7-Year-Old Child With Down Syndrome and Disruptive Behaviors", Journal of Developmental and Behavioral Pediatrics, 2007, vol. 28, No. 2, pp. 151-154.
Markadieu et al., "Physiology and pathophysiology of SLC12A1/2 transporters", Pflügers Archiv, 2013, vol. 466, No. 1, pp. 91-105.
PCT International Search Report and the Written Opinion, Application No. PCT/EP2014/078561 filed Dec. 18, 2014, dated Mar. 17, 2015.

\* cited by examiner

MODULATORS OF INTRACELLULAR CHLORIDE CONCENTRATION FOR TREATING DOWN SYNDROME

This is a national stage application filed under 35 U.S.C. §371 of international application PCT/EP2014/078561, filed under the authority of the Patent Cooperation Treaty on Dec. 18, 2014, published; which claims the benefit of U.S. Provisional Application Ser. No. 61/919,195, filed on Dec. 20, 2013. The entire disclosures of all the aforementioned applications are expressly incorporated herein by reference for all purposes.

FIELD OF INVENTION

The present invention relates to the treatment of Down syndrome. More specifically, the present invention relates to the treatment of Down syndrome in a subject in need thereof, wherein said treatment comprises modulating the intracellular level of chloride, such as, for example, by administering to the subject a modulator of a chloride transporter.

BACKGROUND OF INVENTION

Down syndrome is one of the most common inborn causes of intellectual disability. Down syndrome, also known as trisomy 21, is a genetic disorder caused by the presence of all or part of a third copy of chromosome 21.

In addition to various physical characteristics, Down syndrome is often, though not always, characterized by varying degrees of cognitive impairment, impairment in memory, learning capacity or both. While advances in teaching methods and a trend toward educational mainstreaming has led to an improvement in cognitive development in those who have Down syndrome, there remain constitutive impairments that cannot be fully addressed through pedagogic methodology alone.

Attempts at elaborating drugs for enhancing cognitive function in Down syndrome patients have been made. For example, piracetam is widely used as a purported means of improving cognitive function in children with Down syndrome. However, neither cognitive nor behavioral measures demonstrated improvement under piracetam, and at doses associated with adverse effects (Lobaugh N J et al. Arch Pediatr Adolesc Med. 2001; 155(4):442-448).

WO 2011/086126 A1 discloses a compound which inhibits the importation of chloride into neurons or a compound which improve the outflow of chloride from neurons for use in the treatment of autism; more specifically, the compound claimed is a diuretic and, in particular, bumetanide.

EP2298296 discloses the use of inverse agonist for GABAA receptors to enhance cognitive function.

Despite continued work, no notable medical treatments for Down syndrome have been forthcoming. Therefore, there is a need for alternative targets to improve cognitive/memory deficits related to Down syndrome.

The present invention thus relates to the use of a modulator of intracellular chloride levels, in particular inhibitor of chloride transporters for treating Down syndrome in a subject in need thereof.

DEFINITIONS

In the present invention, the following terms have the following meanings:

"Treatment" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject is successfully "treated" for Down syndrome if, after receiving an effective amount of a modulator according to the present invention, the subject shows observable and/or measurable reduction in or absence of one or more of the following: reduction in one or more of the symptoms associated with the Down syndrome; and improvement in quality of life issues. The above parameters for assessing successful treatment and improvement in the disease are readily measurable by routine procedures familiar to a physician.

"Effective amount" refers to the level or amount of agent that is aimed at, without causing significant negative or adverse side effects to the target, (1) delaying or preventing the onset of Down syndrome; (2) slowing down or stopping the progression, aggravation, or deterioration of one or more symptoms of Down syndrome; (3) bringing about ameliorations of the symptoms of Down syndrome; (4) reducing the severity or incidence of Down syndrome; or (5) curing the Down syndrome. An effective amount may be administered at an early age of Down syndrome, for reducing future impartment. Alternatively or additionally, the effective amount may be administered after long time, for a therapeutic action in adults subjects.

"Pharmaceutically acceptable excipient" refers to an excipient that does not produce an adverse, allergic or other untoward reaction when administered to an animal, preferably a human. It may include any and all solvents, dispersion media, coatings, antibacterial and antifungal agents, isotonic and absorption delaying agents and the like. For human administration, preparations should meet sterility, pyrogenicity, and general safety and purity standards as required by FDA Office of Biologics standards.

"Subject" refers to a mammal, preferably a human. In one embodiment, the term "healthy subject" refers to a subject not diagnosed with Down syndrome. In one embodiment, a "healthy subject" does not present symptoms and/or clinical signs of Down syndrome.

"Modulator" refers to a compound that modulates intracellular chloride level. Preferably, a modulator is a compound whose administration leads to a decrease of intracellular chloride concentration. In one embodiment, said modulator acts on the gene and/or protein expression and/or cell surface expression of a chloride transporter and/or on the activity of a chloride transporter.

"Selective modulator" refers to a selective inhibitor.

"Inhibitor" refers to refers to a natural or synthetic compound that has a biological effect to inhibit or significantly reduce or down-regulate the expression of a gene and/or a protein or that has a biological effect to inhibit or significantly reduce the biological activity of a protein. Consequently, "a NKCC inhibitor" refers to a natural or synthetic compound that has a biological effect to inhibit or significantly reduce or down-regulate the expression of the gene encoding for NKCC and/or the expression of the NKCC protein and/or the biological activity of NKCC.

"Selective inhibitor" refers to that the affinity of the inhibitor for the chloride transporter for instance NKCC is at least 10-fold, 25-fold, 50-fold, 75-fold, 80-fold, 90-fold, 95 fold, 100-fold, 125-fold, 150-fold, 200-fold, 250-fold, 300-fold, 350fold, 400-fold, 450-fold, preferably 500-fold higher than the affinity for the other chloride transporters in particular KCC2.

"About": preceding a figure means plus or less 10% of the value of said figure.

"Analog" refers broadly to the modification or substitution of one or more chemical moieties on a parent compound and may include functional derivatives, positional isomers, tautomers, zwitterions, enantiomers, diastereomers, racemates, isosteres or stereochemical mixtures thereof.

"Functional derivative" refers to a compound which possesses the capacity to modulate the concentration of chloride into neurons (inhibits the importation or activates the outflow of chloride).

DETAILED DESCRIPTION

The present invention relates to a modulator of a chloride transporter for use in the treatment of Down syndrome.

In one embodiment of the invention, treatment of the Down syndrome comprises the administration of an effective amount of a modulator of a chloride transporter to a subject presenting Down syndrome.

In one embodiment of the invention, the modulator of intracellular chloride concentration is a modulator of a chloride transporter.

In one embodiment of the invention, the modulator of intracellular chloride concentration is a selective modulator of a chloride transporter.

In one embodiment, the modulator of a chloride transporter inhibits the importation of chloride into neurons, preferably through the inhibition of transporters involved in the importation of chloride into neurons.

In one embodiment of the invention, said modulator is an inhibitor of the chloride transporter involved in the importation of chloride into neurons.

In one embodiment of the invention, said modulator is an inhibitor of the protein and/or gene expression of a transporter involved in the importation of chloride into neurons.

In an another embodiment of the invention, said modulator is an inhibitor of the protein and/or gene expression of a transporter involved in the importation of chloride into neurons.

Examples of transporters involved in the importation of chloride into neurons include, but are not limited to, NKCC (wherein NKCC stands for "Na—K-2Cl co-transporter"). In one embodiment, the modulator of a chloride transporter is thus an inhibitor of NKCC.

In one embodiment of the invention, the inhibitor of a chloride transporter inhibits the expression of said chloride transporter. Examples of inhibitors of the expression of a chloride transporter include, but are not limited to, siRNAs, shRNAs, antisense oligonucleotide, ribozymes or aptamers of a chloride transporter.

In another embodiment of the invention, the selective inhibitor of a chloride transporter is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L. (Science. 1990; 349(4968): 505-510). The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D. (Clin. Chem. 1999; 45(9):1628-50). Peptide aptamers consists of a conformationally constrained antibody variable region displayed by a platform protein, such as E. coli Thioredoxin A that are selected from combinatorial libraries by two hybrid methods (Colas et al., Nature. 1996; 380(6574):548-50).

Then after raising aptamers directed against the chloride transporter as above described, the skilled man in the art can easily select those blocking chloride importation.

Inhibitors of chloride transporter gene expression for use in the present invention may be based on anti-sense oligonucleotide constructs. Anti-sense oligonucleotides, including anti-sense RNA molecules and anti-sense DNA molecules, would act to directly block the translation of chloride transporter mRNA by binding thereto and thus preventing protein translation or increasing mRNA degradation, thus decreasing the level of chloride transporter, and thus activity, in a cell. For example, antisense oligonucleotides of at least about 15 bases and complementary to unique regions of the mRNA transcript sequence encoding chloride transporter can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of chloride transporter gene expression for use in the present invention. Chloride transporter gene expression can be reduced by contacting a subject or cell with a small double stranded RNA (dsRNA), or a vector or construct causing the production of a small double stranded RNA, such that chloride transporter gene expression is specifically inhibited (i.e. RNA interference or RNAi). Methods for selecting an appropriate dsRNA or dsRNA encoding vector are well known in the art for genes whose sequence is known (e.g. see Tuschl, T. et al. Genes Dev. 1999; 13(24):3191-7; Elbashir, S. M. et al. Nature. 2001; 411(6836):494-8.; Hannon, G J. Nature. 2002; 418(6894):244-51; McManus, M T. et al. Nat Rev Genet. 2002; 3(10):737-47; Brummelkamp, T R. et al. Science. 2002; 296(5567):550-3; U.S. Pat. Nos. 6,573,099 and 6,506,559; and International Patent Publication Nos. WO 01/36646, WO 99/32619, and WO 01/68836).

Ribozymes can also function as inhibitors of chloride transporter gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of chloride transporter mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of chloride transporter gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing a chloride transporter. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler M. (Methods Enzymol. 1990; 185:512-27).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., (Molecular cloning: a laboratory manual. New York: Cold Spring Harbor Laboratory Press, 1989). In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In another embodiment, the inhibitor of a chloride transporter inhibits the activity of the chloride transporter. Examples of such inhibitors include, but are not limited to, small molecules, antibodies, minibodies, diabodies or fragments thereof binding to the chloride transporter, and antagonists of the chloride transporter.

In another embodiment, the inhibitor of the invention is an antibody (the term including antibody fragment) that can block the activity of a transporter involved in the importation of chloride into neurons.

In particular, the inhibitor of the invention may consist in an antibody directed against a transporter involved in the importation of chloride into neurons.

Antibodies directed against said transporter can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against said transporter can be prepared and isolated using any technique that provides for the production of antibody molecules by continuous cell lines in culture. Techniques for production and isolation include but are not limited to the hybridoma technique originally described by Köhler and Milstein (Nature. 1975; 256(5517):495-7); the human B-cell hybridoma technique (Cote et al., Proc Natl Acad Sci U S A. 198; 80(7):2026-30); and the EBV-hybridoma technique (Cole et al., Mol Cell Biochem. 1984; 62 (2):109-20). Alternatively, techniques described for the production of single chain antibodies (see e.g. U.S. Pat. No. 4,946,778) can be adapted to produce anti-modulator, or anti-modulator ligands single chain antibodies. Chloride transporter inhibitor useful in practicing the present invention also include anti-modulator, or anti-modulator ligands antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to said transporter.

In another embodiment, the inhibitor of the invention can include isomers, tautomers, zwitterions, enantiomers, diastereomers, racemates, or stereochemical mixtures thereof. Inhibitors of the present invention can also comprise isosteres.

The term "isosteres" as used herein broadly refers to elements, functional groups, substituents, molecules, or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Other physical properties that isosteric compounds usually share include boiling point, density, viscosity, and thermal conductivity. However, certain properties are usually different: dipolar moments, polarity, polarization, size, and shape since the external orbitals may be hybridized differently.

The term "isomers" as used herein refers broadly to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure can exist in some of the compounds of the present invention, which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. Such compounds can also be prepared or isolated as pure stereoisomers, i.e., as individual enantiomers or diastereomers, or as stereoisomer-enriched mixtures. Tautomers are readily inter-convertible constitutional isomers and there is a change in connectivity of a ligand, as in the keto and enol forms of ethyl acetoacetate (including tautomers of any said compounds.) Zwitterions are inner salts or dipolar compounds possessing acidic and basic groups in the same molecule. At neutral pH, the cation and anion of most zwitterions are equally ionized.

In one embodiment, said inhibitor is a selective NKCC inhibitor.

In one embodiment of the invention, said selective inhibitor interacts directly with the chloride transporter.

In one embodiment, said selective inhibitor is an antagonist of a chloride transporter importing chloride into neurons.

In one embodiment of the invention, the inhibitor of a chloride transporter is an inhibitor of NKCC, such as, for example, a diuretic (such as, for example, a loop diuretic); or a NKKC antagonist.

In one embodiment of the invention, the selective inhibitor decreasing the gene and/or protein expression and/or activity of the chloride co-transporter NKCC, has a low affinity for KCC2.

In one embodiment of the invention, the selective inhibitor of the chloride transporter has an affinity for KCC2 inferior than 10M, preferably 10M, more preferably less than 10M.

In another embodiment of the invention, the selective inhibitor of the chloride transporter has an affinity at least much higher to NKCC than to KCC2 (of at least 1 order of magnitude, preferably of at least 2 orders of magnitude, more preferably of at least 3 orders of magnitude and most preferably of at least 4 orders of magnitude).

In another embodiment of the invention, the selective inhibitor of the chloride transporter does not bind to KCC2 at all.

In one embodiment of the invention, the selective inhibitor of the chloride transporter refers to a molecule that has an affinity for the NKCC at least 10-fold, 25-fold, 50 fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than its affinity for any one of other isoforms of KCC transporters comprising KCC1, KCC2, KCC3, KCC4, other transporter chloride including in a non-limiting list: Cl—HCO3-transporter.

Examples of inhibitors of a chloride transporter, preferably of NKCC, include, but are not limited to, bumetanide, furosemide, ethacrynic acid, torsemide, azosemide, muzolimine, piretanide, tripamide and analogs, functional derivatives and prodrugs of such compounds; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs, functional derivatives and prodrugs of such compounds.

Examples of analogs of bumetanide include, but are not limited to: bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)$_{n-1}$-ethyl ester, bumetanide benzyltrimethyl-ammonium salt, bumetanide cetyltrimethylammonium salt, pivaloyloxymethyl ester of bumetanide, methyl ester of bumetanide, N,N-dimethylaminoethyl ester of bumetanide, bumetanide [—(C=O)—SH] thioacid, bumetanide S-methyl thioester, bumetanide S-cyanoethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S—(N,N-diethylglycolamido) thioester, bumetanide S—(N,N-dimethylglycolamido) thioester, bumetanide S-pivaxetil thioester, bumetanide S-propaxetil thioester, bumetanide S-(methoxyipolyethyleneoxy)$_{n-1}$-ethyl] thioester, bumetanide [—(C=O)—S⁻] benzyltrimethyl-ammonium thioacid salt and bumetanide [—(C=O)—S] cetyltrimethylammonium thioacid salt; metastable bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl) thioester, bumetanide O-[3(dimethylaminopropyl) thioester, bumetanide O—(N,N-diethylglycolamido) thioester, bumetanide O-pivaxetil thioester, bumetanide O-propaxetil thioester, bumetanide O[methoxy(polyethyleneoxy)$_{n-1}$ ethyl] thioester, bumetanide [—(C=S)—O—] benzyltrimetylammonium thioacid salt and bumetanide [—(C=S)—O—] cetyltrimethylammonium thioacid salt.

Examples of analogs of furosemide include, but are not limited to: furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)$_{n-1}$-ethyl ester, furosemide pivaxetil ester, furosemide propaxetil ester, furosemide benzyltrimethylammonium acid salt and furosemide cetyltrimethylammonium acid salt, furosemide [—(C=O)—SH] thioacid, furosemide S-methyl thioester, furosemide S-cyanomethyl thioester, furosemide S-ethyl thioester, furosemide S-isoamyl thioester, furosemide S-octyl thioester, furosemide S-benzyl thioester, furosemide S-(morpholinoethyl) thioester, furosemide S-[3-(dimethylaminopropyl)] thioester, furosemide S—(N,N-diethylglycolamido) thioester, furosemide S—(N,N-dimethylglycolamido) thioester, furosemide S-pivaxetil thioester, furosemide S-propaxetil thioester, furosemide S-[methoxy(polyethyleneoxy)$_{n-1}$-ethyl] thioester, furosemide [—(C=O)—S⁻] benzyltrimethylammonium thioacid salt and furosemide [(C=O)—S⁻] cetyltrimethylammonium thioacid salt, metasta-stable furosemide [—(C=S)OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl) thioester, furosemide O-[3-(dimethylaminopropyl)] thioester, furosemide 0-(N,Ndiethylglycolamido) thioester, furosemide O—(N,N-dimethylglycolamido) thioester, furosemide O-pivaxetil thioester, furosemide O-propaxetil thioester, furosemide O[methoxy(polyethyleneoxy)n-1-ethyl] thioester, furosemide [—(C=S)—O⁻] benzyltrimethylammonium thioacid salt and furosemide [—(C=S)—O⁻] cetyltrimethylammonium thioacid salt; furosemide thioaldehyde, furosemide [—(C=S)—SH] dithioacid, furosemide methyl dithioester, furosemide cyanomethyl dithioester, furosemide ethyl dithioester, furosemide isoamyl di-thioester, furosemide octyl dithioester, furosemide benzyl dithioester, furosemide dibenzyl-thioamide, furosemide diethyl-thioamide, furosemide morpholinoethyl dithioester, furosemide 3-(dimethylaminopropyl) dithioester, furosemide N,N-diethylglycolamido dithioester, furosemide N,N-dimethylglycolamido dithioester, furosemide pivaxetil dithioester, furosemide propaxetil dithioester, furosemide methoxy(polyethyleneoxy)$_{n-1}$ ethyl dithioester, furosemide benzyltrimethylammonium dithioacid salt and furosemide cetyltrimethylammonium dithioacid salt.

Examples of analogs of piretanide include, but are not limited to: piretanide aldehyde, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzyltrimethylammonium salt, piretanide cetyltrimethylarnrnonium salt, piretanide N,N-dimethylglycolamide ester, piretanide methoxy(polyethyleneoxy)$_{n-1}$-ethyl ester, piretanide pivaxetil ester, piretanide propaxetil ester, piretanide [—(C=O)—SH] thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl) thioester, piretanide S-[3(dimethylaminopropyl)] thioester, piretanide S—(N,N-diethylglycolamido) thioester, piretanide S—(N,N-dimethylglycolamido) thioester, piretanide S-pivaxetil thioester, piretanide S-propaxetil thioester, piretanide S-[methoxy(polyethyleneoxy)$_{n-1}$ ethyl] thioester, piretanide [—(C=O)—S⁻] benzyltrimethylammonium thioacid salt and piretanide [—(C=O)—S⁻] cetyltrimethylammonium thioacid salt; metastable piretanide [—(C=S)—OH] thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl) thioester, piretanide O-[3-(dimethylaminopropyl)] thioester, piretanide O—(N,N-diethylglycolamido) thioester, piretanide, O—(N,N-dimethylglycolamido) thioester, piretanide O-pivaxetil thioester, piretanide O-propaxetil thioester, piretanide O-[methoxy(polyethyleneoxy)$_{n-1}$ ethyl] thioester, piretanide [—(C=S)—O⁻] benzyltrimethylammonium thioacid salt and piretanide [—(C=S)—O⁻] cetyltrimethylammonium thioacid salt; piretanide thioaldehyde, piretanide [—(C=S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethyl-thioamide, piretanide morpholinoethyl dithioester, piretanide 3-(dimethylaminopropyl) di-thioester, piretanide N,N-diethylglycolamido dithioester, piretanide N,N-dimethylglycolamido dithioester, piretanide pivaxetil dithioester, piretanide propaxetil dithioester, piretanide methoxypolyethyleneoxyethyl dithioester, piretanide benzyl-trimethylammonium dithioacid salt and piretanide cetyltrimethylarnmoniurn dithioacid salt.

Examples analogs of azosemide include, but are not limited to: tetrazolylsubstituted azosemides (such as methoxymethyl tetrazolyl-substituted azosemides, methylthiomethyl tetrazolyl-substituted azosemides, N-mPEG350-tetrazolyl-substituted azosemides), azosemide benzyltrimethylammoniurn salt, azosemide cetyltrimethylammonium salt, pyridine-substituted torsemide quaternary ammonium salts or the corresponding inner salts (zwitterions), methoxymethyl pyridinium torsemide salts, methylthioethyl pyridinium torsemide salts and N-mPEG350pyridinium torsemide salts.

In another embodiment, an analog of an inhibitor according to the invention may have a formula as described in the patent application WO2006/110187. Examples of said analogs include, but are not limited to, compounds of general formula I, II and/or III:

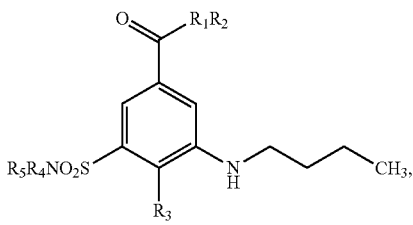

(I)

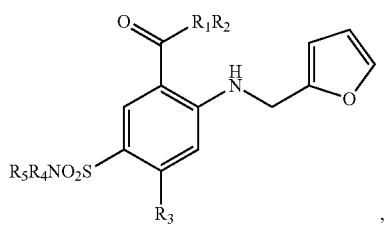

(II)

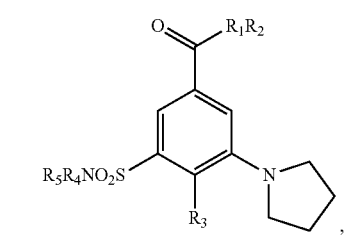

(III)

or a pharmaceutically acceptable salt, solvate, tautomer or hydrate thereof, wherein R1 is not present, H or O;

R2 is H or when R1 is O, is selected from the group consisting of: alkylaminodialkyl, alkylaminocarbonyldialkyl, alkyloxycarbonylalkyl, alkylaldehyde, alkylketoalkyl, alkylamide, an alkylammonium group, alkylcarboxylic acid, alkylheteroaryls, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkylalkyl and methylthioalkaryl, unsubstituted or substituted, and when R1 is not present, R2 is selected from the group consisting of: hydrogen, dialkylamino, diarylamino, dialkylaminodialkyl, dialkylcarbonylaminodialkyl, dialkylesteralkyl, dialkylaldehyde, dialkylketoalkyl, dialkylamido, dialkylcarboxylic acid, and dialkylheteroaryls, unsubstituted or substituted;

R3 is selected from the group consisting of: aryl, halo, hydroxy, alkoxy, and aryloxy, unsubstituted or substituted; and R4 and R5 are each independently selected from the group consisting of: hydrogen, alkylaminodialkyl, alkylhydroxyaminodiakyl, unsubstituted or substituted.

Another non-limiting example of said analogs of an inhibitor of the invention is a compound of general formula IV

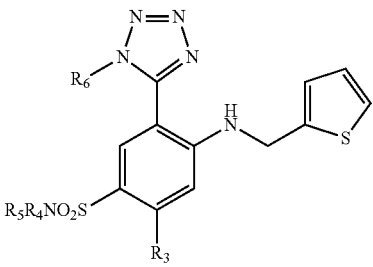

(IV)

or a pharmaceutically acceptable salt, solvate, tautomer or hydrate thereof, wherein R3, R4 and R5 are as defined above; and R6 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted.

Another non-limiting example of said analogs is a compound of general formula V

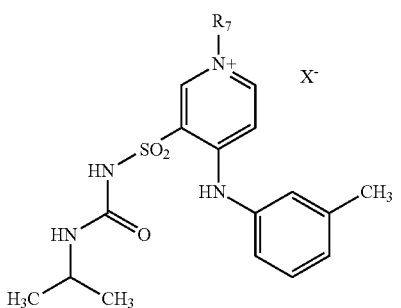

(V)

or a pharmaceutically acceptable salt, solvate, tautomer or hydrate thereof, wherein R7 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted; and X— is a halide such as bromide, chloride, fluoride, iodide or an anionic moiety such as mesylate or tosylate; alternatively, X— is not present and the compound forms an "inner" or zwitterionic salt by loss of a proton from the sulfonylurea moiety (—SO2-NH—CO—).

The term "alkyl" as used herein refers to a straight or branched chain saturated or partially unsaturated hydrocarbon radical, wherein by "unsaturated" is meant the presence of 1, 2 or 3 double or triple bonds, or a combination thereof. Examples of alkyl groups include, but are not limited to, methyl, ethyl, isopropyl, tert-butyl, n-pentyl and the like.

The term "alkylene" as used herein refers to a straight or branched chain having two terminal monovalent radical centers derived by the removal of one hydrogen atom from each of the two terminal carbon atoms of straight-chain parent alkane.

The term "aryl" as used herein refers to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

The term "halo" as used herein refers to bromo, chloro, fluoro or iodo. Alternatively, the term "halide" as used herein refers to bromide, chloride, fluoride or iodide.

The term "hydroxyl" as used herein refers to the group —OH.

The term "alkoxy" as used herein alone or as part of another group, refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like.

The term "aryloxy" as used herein refers to the group —ArO wherein Ar is aryl or heteroaryl. Examples include, but are not limited to, phenoxy, benzyloxy and 2-naphthyloxy.

The term "amino" as used herein refers to —NH2 in which one or both of the hydrogen atoms may optionally be replaced by alkyl or aryl or one of each, optionally substituted.

The term "alkylthio" as used herein alone or as part of another group, refers to an alkyl group, as defined herein, appended to the parent molecular moiety through a sulfur moiety. Representative examples of alkylthio include, but are not limited to, methylthio, ethylthio, n-propylthio, isopropylthio, n-butylthio, and the like.

The term "carboxy" as used herein refers to the group —CO2H.

The term "quaternary ammonium" as used herein refers to a chemical structure having four bonds to the nitrogen with a positive charge on the nitrogen in the "onium" state, i.e., "R4N$^+$" or "quaternary nitrogen", wherein R is an organic substituent such as alkyl or aryl. The term "quaternary ammonium salt" as used herein refers to the association of the quaternary ammonium with a cation.

The term "substituted" as used herein refers to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, ureido and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent.

The term "solvate" as used herein is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, isopropanol, ethanol, methanol, DMSO, ethyl acetate, acetic acid, or ethanolamine.

The term "hydrate" as used herein refers to the compound when the solvent is water.

In another embodiment, an analog of an inhibitor of the chloride transporter according to the invention may have a formula as described in the patent application WO2012/018635.

Examples of said analogs include but are not limited to a compound of formula:

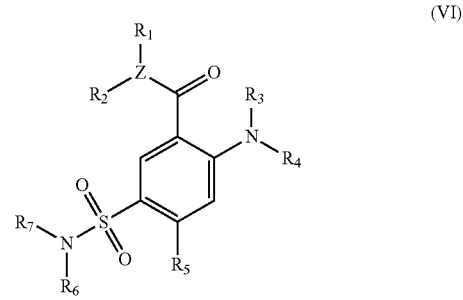

(VI)

or a pharmaceutically acceptable salt thereof, wherein:

Z is oxygen or nitrogen;

R1 and R2 are each independently hydrogen, alkyl, aryl, arylalkyl, heteroaryl, heteroaryl alkyl, heterocyclo alkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents; R5 is halo, aryl, aryloxy, arylamino, heteroarylamino, heterocycloalkyl, heteroaryl, heteroaryloxy, heterocycloalkoxy, or alkythio; and R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents.

Examples of said analogs include but are not limited to a compound of formula:

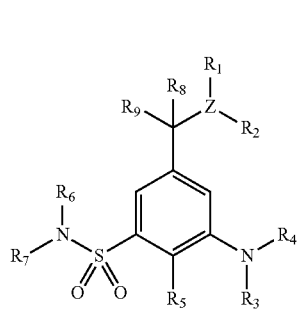

(VII)

or a pharmaceutically acceptable salt thereof, wherein:
Z is oxygen or nitrogen;
R1 and R2 are each independently hydrogen, alkyl, aryl, arylalkyl, heteroaryl, heteroarylalky], heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;
R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents; R5 is alkoxy, halo, aryl, aryloxy, alkaryloxy, arylamino, heteroarylamino, heterocycloalkyl, heteroaryl, hetero ryloxy, heterocycloalkoxy, or alkythio;
R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and
R8 and R9 are each independently hydrogen, alkyl, or R8 and R9 together with the atom to which they are attached, form a 3-6 membered substituted or unsubstituted cycloalkyl or heterocycloalkyl ring.

Examples of said analogs include but are not limited to a compound of formula:

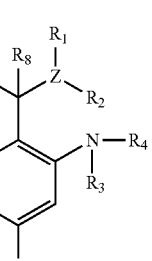

(VIII)

or a pharmaceutically acceptable salt thereof, wherein:
Z is oxygen or nitrogen;
R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalkyl, or R3 and R4, together with the atom to which they are attached, form a 4-7 membered heterocyclic ring that can have one or more additional heteroatoms and can have one or more substituents; R5 is alkoxy, halo, aryl, aryloxy, alkaryloxy, arylamino, heteroarylamino, heterocycloalkyl, heteroaryl, heteroaryloxy, heterocycloalkoxy, or alkythio;
R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and
R8 and R9 are each independently hydrogen, alkyl, or R8 and R9 together with the atom to which they are attached, form a 3-6 membered substituted or unsubstituted cycloalkyl or heterocycloalkyl ring.

In another embodiment, an analog of the inhibitor of the chloride transporter may have a formula as described in the patent applications incorporated herein US2007/0155729, GB2207129, in U.S. Pat. Nos. 4,247,550; 3,985,777; 7,282, 519.

In another embodiment, an alternative inhibitor of NKCC activity is selected from the group comprising non-diuretic compounds: protein kinase inhibitors staurosporine and K252a, through SPAK autophosphorylation and substrate phosphorylation of the co-transporter, or the sulfhydryl agents N-ethylmaleimide (NEM) and diamide (Gagnon et al. 2006 Mol. Cell. Biol. 26(2):689-698).

Preferably, the modulator of the intracellular chloride level is bumetanide, analogs, functional derivatives and prodrugs thereof.

In one embodiment of the invention, the effective amount of a modulator of intracellular chloride concentration corresponds to the amount to be administered to a subject in need thereof for reaching the intracellular chloride concentration measured in a healthy subject.

In one embodiment of the invention, the effective amount of a modulator ranges from about 0.01 mg to about 500 mg, preferably from about 0.05 mg to about 100 mg, more preferably from about 0.1 mg to about 10 mg and even more preferably from about 0.5 mg to about 1.5 mg.

The present invention also relates to a pharmaceutical composition for use in the treatment of Down syndrome in a subject in need thereof, wherein said pharmaceutical composition comprises an effective amount of a modulator of intracellular chloride concentration and at least one pharmaceutically acceptable excipient.

Another object of the invention is a medicament for use in the treatment of Down syndrome comprising an effective amount of a modulator of intracellular chloride concentration.

The composition, pharmaceutical composition or medicament may be administered by several routes of administration. Examples of adapted routes of administration include, but are not limited to: subcutaneous, intramuscular, intravenous, intraocular, transdermal, topical, parenteral, intranasal and oral administration, or injection, preferably in utero injection. The type of form for administration will be matched to the severity of the syndrome as well as to the age, weight, sex of the subject to be treated.

In one embodiment, the composition, pharmaceutical composition or medicament of the invention is in a form adapted for injection, preferably selected from the group comprising solutions, such as, for example, isotonic solution, saline solution, sterile aqueous solutions; dispersions, emulsions, suspensions, solid forms suitable for using to prepare solutions or suspensions upon the addition of a liquid prior to use, such as, for example, powder, freeze-dried compositions, liposomal forms and the like.

In one embodiment, the composition, pharmaceutical composition or medicament of the invention is in a form adapted to oral administration. In one embodiment, the form adapted to oral administration is a solid form selected from the group comprising tablets, pills, capsules, soft gelatin capsules, sugarcoated pills, orodispersing tablets, effervescent tablets or other solids. In another embodiment, the form adapted to oral administration is a liquid form, such as, for example, a drinkable solution, a buccal spray, liposomal forms and the like.

In one embodiment, the composition, pharmaceutical composition or medicament of the invention is in a form adapted for local delivery via the nasal and respiratory routes. Examples of formulations suitable for nasal administration include but are not limited to, nasal solutions, sprays, aerosols and inhalants.

In one embodiment, the composition, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

In one embodiment, the composition, pharmaceutical composition or medicament of the invention is in the form of, or comprises, liposomes and/or nanoparticles.

In one embodiment, the composition, pharmaceutical composition or medicament of the invention further comprises some excipients, such as, for example, surfactants (e.g. hydroxypropylcellulose); suitable carriers, such as, for example, solvents and dispersion media containing, for example, water, monosodium or disodium phosphate, sodium, potassium, calcium or magnesium chloride, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

In one embodiment of the invention, the composition, pharmaceutical composition or medicament of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

The present invention can also use a prodrug of the modulator of the intracellular chloride concentration within neurons or an encapsulation of said modulator.

In one embodiment, the invention uses a prodrug of the modulator of intracellular chloride concentration within neurons.

In another embodiment, the invention uses a prodrug of the inhibitor of chloride importation within neurons.

Prodrugs as described herein are capable of passage across the blood-brain barrier and may undergo hydrolysis by CNS esterases to provide the active compound.

Prodrugs provided herein may also exhibit improved bioavailability, improved aqueous solubility, improved passive intestinal absorption, improved transporter-mediated intestinal absorption, protection against accelerated metabolism, tissue-selective delivery, less (or fewer) side effects, lessened or no deleterious drug interaction with other medications, and/or passive enrichment in the target tissue.

The term "prodrug" as used herein refers to a compound that is converted under physiological conditions, by solvolysis or metabolically to a specified compound that is pharmaceutically/pharmacologically active. The "prodrug" can be a compound as defined herein that has been chemically derivatized such that it retains some, all or none of the bioactivity of its parent drug compound and is metabolized in a subject to yield the parent drug compound. The prodrug of the present invention may also be a "partial prodrug" in that the compound has been chemically derivatized such that it retains some, all or none of the bioactivity of its parent drug compound and is metabolized in a subject to yield a biologically active derivative of the compound.

Prodrugs can be formed by attachment of biocompatible polymers, such as those previously described including polyethylene glycol (PEG), to compounds of the present invention using linkages degradable under physiological conditions. See also Schacht, et al. (1997) Poly(ethylene glycol) Chemistry and Biological Applications, American Chemical Society, San Francisco, Calif. 297-315. Attachment of PEG to proteins can be employed to reduce immunogenicity and/or extend the half-life of the compounds provided herein. Any conventional PEGylation method can be employed, provided that the PEGylated agent retains at least some pharmaceutical activity.

In one embodiment, the selective inhibitor used in the invention is bumetanide-PEGylated.

In one embodiment, the present invention uses prodrugs comprising the compounds described herein. The prodrugs can be formed utilizing a hydrolyzable coupling to the compounds described herein. Ettmayer, et al. (2004) J. Med. Chem. 47(10): 2394-2404; Testa and Mayer (2003) Hydrolysis in Drug and Prodrug Metabolism: Chemistry, Biochemistry and Enzymology Wiley-Verlag Helvetica Chimica Acta, Zuerich (Chapters 1-1): 1-780.

In one embodiment, the modulator of a chloride transporter is administered only once.

In one embodiment, the modulator of a chloride transporter is administered at least once a day, preferably twice a day, more preferably at least three times a day.

In one embodiment, the daily amount of a modulator to be administered to a subject ranges from about 0.01 mg/day to about 500 mg/day, preferably from about 0.05/day mg to about 100 mg/day, more preferably from about 0.1 mg/day to about 10 mg/day and even more preferably from about 0.5 mg/day to about 1.5 mg/day.

In another embodiment, the administration dose of the modulator of a chloride transporter is determined by the skilled artisan and personally adapted to each subject.

In one embodiment, the modulator is administered in a sustained-release form.

In one embodiment, the modulator of a chloride transporter is formulated in a composition which comprises a delivery system that controls the release of the modulator. Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, brasiliensis, polydienes, and halogenated natural and synthetic rubbers; and flexible thermoset resins such as polyurethanes, epoxy resins; biodegradable polymers and the like.

In another embodiment, the modulator is administered in combination with other therapies that could include: speech therapy, behavioral therapy, sensory integration occupational therapy, special education, or individualized educational plans, and, when necessary, treatment of physical abnormalities.

In one embodiment, the modulator of a chloride transporter is used for treating behavioral and/or cognitive symptoms associated with Down syndrome. In one embodiment, the administration to a subject in need thereof of the modulator of a chloride transporter according to the invention results in the alleviation of behavioral symptoms of Down syndrome.

In one embodiment, the modulator of a chloride transporter is used for treating synaptic defects/symptoms associated with Down syndrome. In one embodiment, the administration to a subject in need thereof of the modulator of a chloride transporter according to the invention results in the alleviation of synaptic defects associated with Down syndrome.

Examples of synaptic defects/symptoms associated with an Down syndrome include, but are not limited to, defective synaptic morphology (such as, for example, an abnormal number, length, and/or width of dendritic spines) and defective synaptic function (such as, for example, enhanced long-term depression (LTD) and/or reduced long-term potentiation (LTP)).

In another embodiment of the invention, the modulator of a chloride transporter is used for treating synaptic plasticity defects associated with Down syndrome. In one embodiment, the administration to a subject in need thereof of the modulator of a chloride transporter according to the invention results in the alleviation of plasticity defects associated with Down syndrome.

In one embodiment, the subject is a male.
In another embodiment, the subject is a female.
In one embodiment, the subject is an adult.
In one embodiment, the subject is a young child.
In another embodiment, the subject is a new born child.
In one embodiment, the subject is a healthy subject.
In another embodiment, the subject has been diagnosed as having Down syndrome.
In one embodiment, said subject presents a familial history of Down syndrome.

The present invention also relates to a method for decreasing the intracellular concentration of chloride in a subject in need thereof, preferably the neuronal intracellular concentration of chloride.

Another object of the invention is a method for modulating the intracellular chloride concentration of a subject in need thereof, wherein the method comprises administering to the subject in need thereof an effective amount of a modulator of a chloride transporter.

In one embodiment of the invention, the method comprises administering to the subject an effective amount of a modulator of a chloride transporter.

In one embodiment of the invention, said effective amount is calculated in order to reach a desired intracellular concentration of chloride.

In one embodiment of the invention, the method comprises administering to the subject in need thereof the composition, the pharmaceutical composition or the medicament of the invention.

EXAMPLES

The present invention is further illustrated by the following examples.

We have obtained experimental evidence linking the co-transporter of chloride NKCC and the diuretic bumetanide with Down syndrome. Using the classical mice model of Down syndrome, we found that mice have as expected affected physiological and behavioral alterations including reduced Long Term Potentiation of synaptic currents and memory and novel object recognition tests. However, we also found that the polarity of the actions of GABA is altered with elevated intracellular chloride levels that lead to depolarizing and occasionally excitatory actions of GABA. This also leads to enhanced ongoing excitatory glutamatergic activity that will perturb spontaneous behaviorally relevant oscillations. A similar situation has been observed in many pathogenic conditions including seizures, epilepsy, spinal cord lesions and various traumatic insults that are also associated with over activity episodes. We therefore tested the effects of a diuretic bumetanide that blocks NKCC and is known to reduce efficiently and specifically intracellular chloride levels. We found that bumetanide restores LTP, hyperpolarizing GABA actions, reduces elevated glutamatergic activity and also rescues the behavioral deficient novel object recognition and memory tests. This drug is therefore efficacious to restores physiological activity and behavioral parameters.

Materials and Methods

Material

Animals

Ts65Dn mice, a murine model of Down syndrome carrying a segmental duplication of part of mouse chromosome 16, orthologous to most of the long arm of human chromosome 21, demonstrate learning and memory deficits, which are hypothetically due to selective decreases in the number of excitatory synapses in the brain rather than gross abnormalities in neuroanatomy. Theoretically, triplicate genes found in the Ts65Dn mice shift the optimal balance of excitation and inhibition in the dentate gyrus (and, possibly, other parts of the brain) to a state in which excessive inhibition obscures otherwise normal learning and memory (Reeves et al., Nature Genetics, 11(2):177-84 (1995)).

Methods

Statistics

For all panels, histograms represent average±SEM, whereas circles indicate data from single cells. Statistical significance: *P<0.05, P<0.01, *P<0.001.

FIG. 1 represents the effect of acute bumetanide on the spontaneous activity in Ts65Dn mice at P15 compared to control values. Whole-cell voltage clamp recordings of spontaneous excitatory postsynaptic currents (sEPSCs) at −70 mV from individual hippocampal CA3 pyramidal neurons in acute neocortical brain slices from P15 Ts65Dn. (A) Representative traces of sEPSCs recorded from Ts65Dn mice in control and in the presence of bumetanide. (B) Average values of frequency of sEPSCs recorded in control mice (n=9), in Ts65Dn mice (n=9) p<0.006 (two-tails two-samples t-test) and with bumetanide application (n=9), *p<0.001 (two-tails paired t-test).

Figure 2:
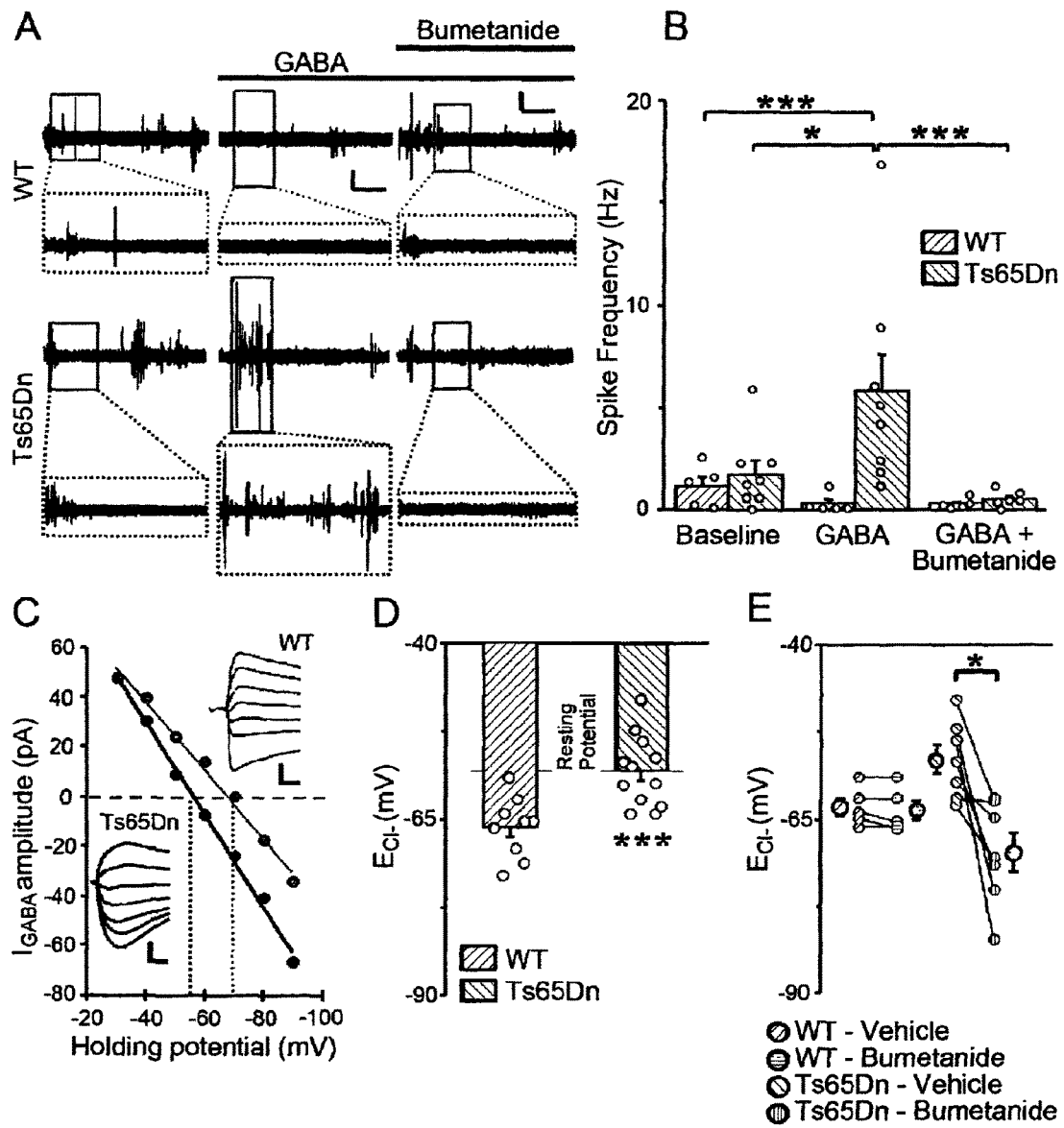

FIG. 2 represents CA1 hippocampal pyramidal neurons that exhibit excitatory responses to GABA and a depolarized EC1 in adult Ts65Dn mice. (A) shows example traces of spontaneous spiking activity from CA1 pyramidal neurons in cell-attached configuration in acute slices derived from Ts65Dn and WT mice at 10-12 weeks of age before (baseline) and during bath application of either GABA (10 µM) or GABA and bumetanide (10 µM). (B) shows bath application of GABA increased spike frequency in Ts65Dn neurons (post hoc Holm-Sidak test following Two-Way ANOVA, P=0.020), and co-treatment with bumetanide reverted this effect (P<0.001). (C) shows example of current-voltage relations of GABA currents (IGABA) elicited by puffing GABA at the neuronal cell body, and recorded by gramicidin perforated patch-clamp configuration in hippocampal slices from Ts65Dn animals (dark grey) and WT littermates (light grey). The vertical dotted lines indicate the value of the reversal potential on the x axis. Insets, sample traces of GABA-induced currents at different holding potentials. Scale bars: vertical, 50 pA; horizontal, 50 ms. (D) shows average EC1 values for Ts65Dn (dark grey) and WT (light grey) neurons recorded as in C. EC1 were significantly more depolarized in Ts65Dn mice than in WT (Student's t-test, P<0.001). Average resting potentials (dotted lines) were not different in Ts65Dn and WT neurons. (E) shows EC1 values before and 20 min after bath application of bumetanide (10 µM) to a subset of cells in D. Bumetanide application rescued the depolarized EC1 in Ts65Dn cells (paired t-test, P=0.012), while leaving those from WT mice unaltered (P>0.05).

Figure 3:
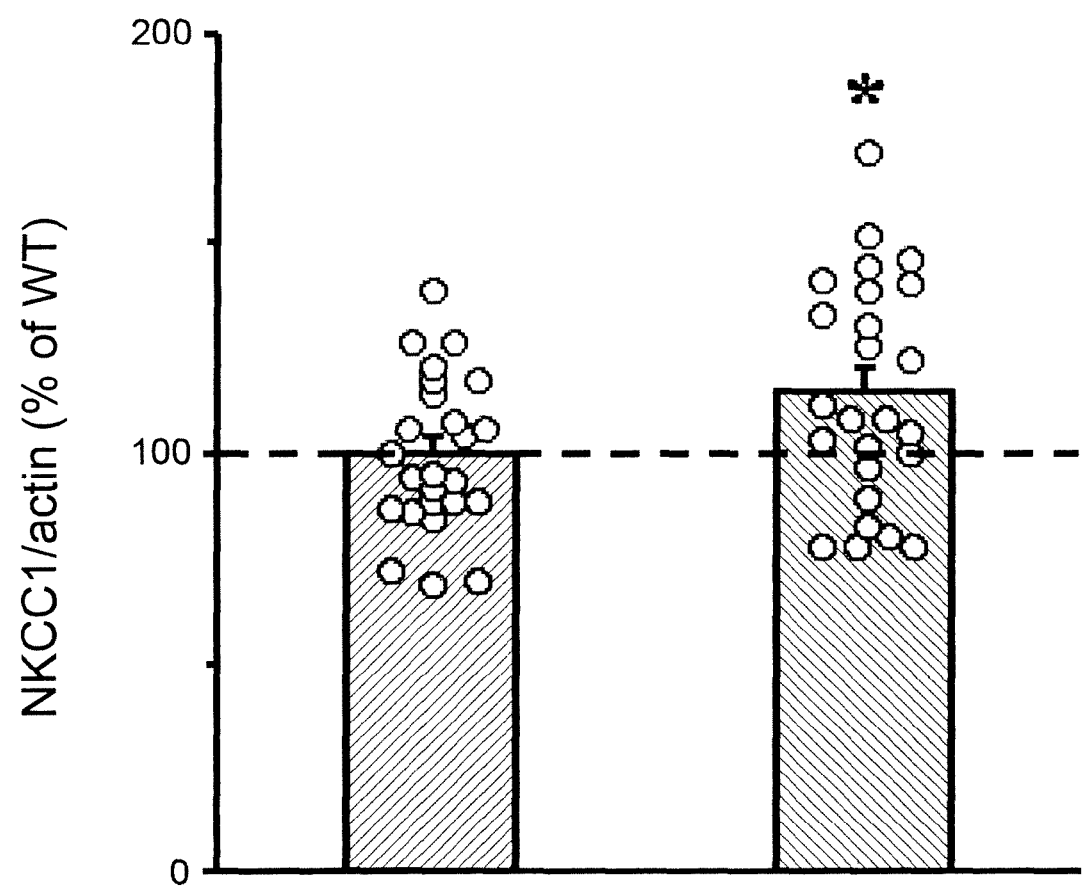

FIG. 3 shows histograms of NKCC protein expression in WT and Ts65Dn mice. (A) shows a higher expression of NKCC (expressed as percentage of WT) in Ts65Dn in comparison to WT (Student's t-test, P=0.025); average±SEM and data from single animals (circles).

Figure 4:
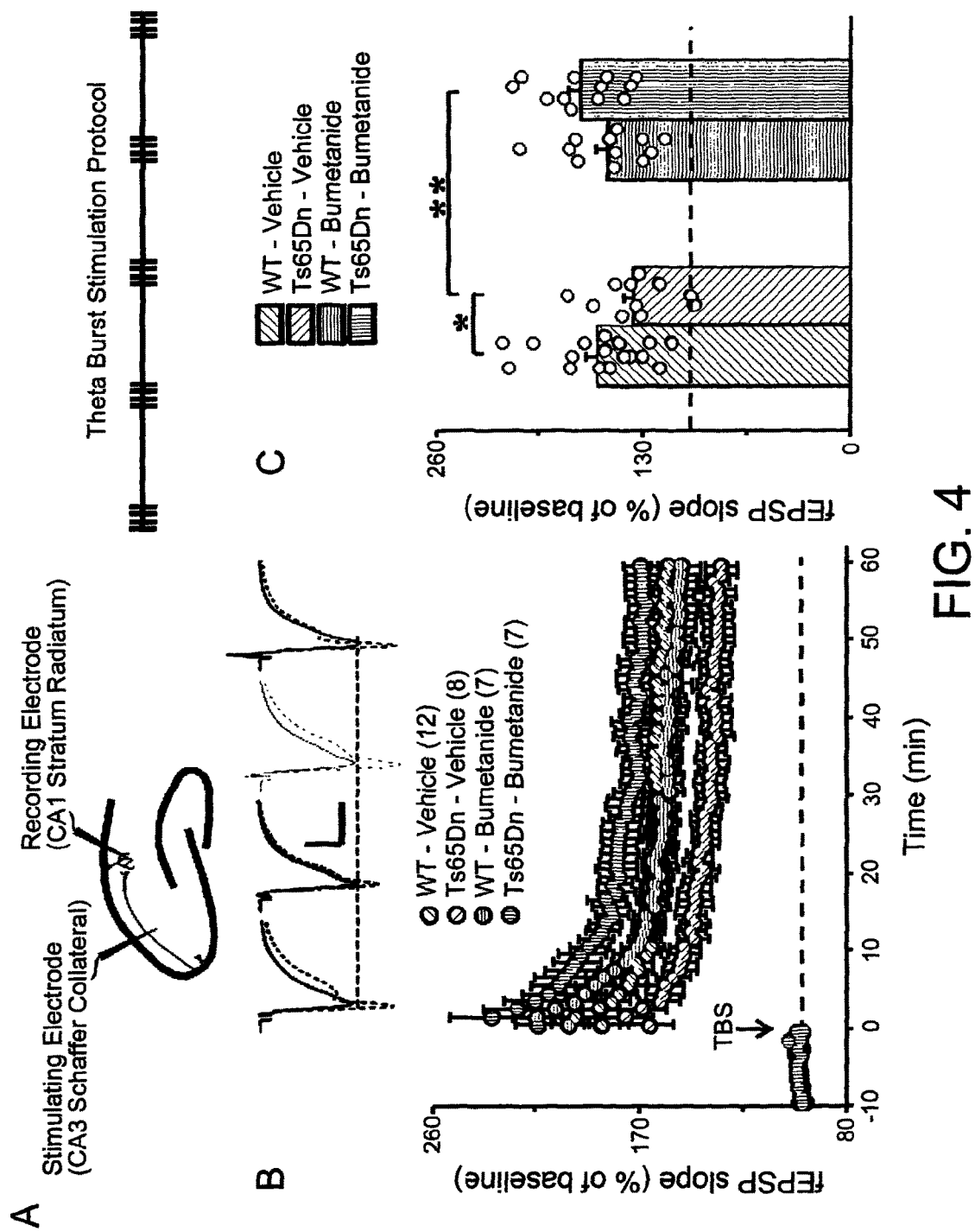

FIG. 4 represents the effect of bumetanide bath application on hippocampal CA3CA1 LTP in Ts65Dn mice. (A) shows sketch of the in vitro recording configuration (left) and stimulation protocol (right). (B) shows average time course of the increase in the slope of the field excitatory postsynaptic potentials (fEPSP) in hippocampal slices during bath application of either vehicle or bumetanide (10 µM). Numbers in parentheses: number of animals utilized. Insets: Average of 10 fEPSP traces recorded for each experimental group before (continuous line) and 60 min after TBS (dashed line). Stimulus artefacts have been deleted from traces for clarity. Scale bars: vertical, 1 mV; horizontal, 10 ms. (C) shows average LTP±SEM (histogram) and single slice cases (circles) of the last 5 min of recordings in B. Ts65Dn slices showed lower LTP in comparison to WT (post hoc Tukey test following Two-Way ANOVA, P=0.038), and bumetanide rescued this deficit (P=0.005).

Figure 5:
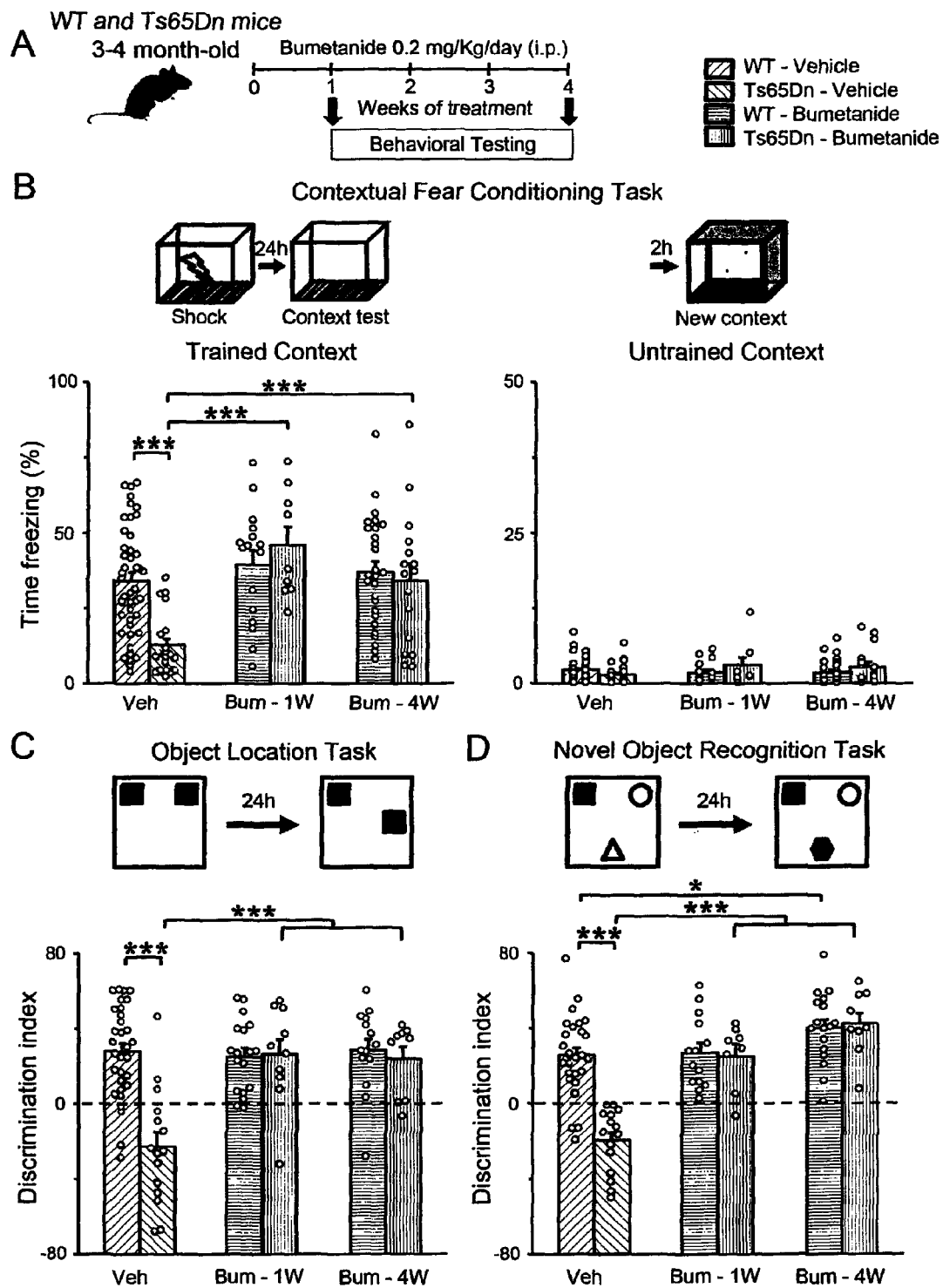

FIG. 5 represents the effect of bumetanide systemic treatment on cognitive functions in behavioral tasks in Ts65Dn mice. (A) shows schematic cartoon of the experimental protocol (left) for the different experimental groups (right). (B) Top, schematic representation of the contextual fear conditioning test. Bottom, Ts65Dn mice showed impaired associative memory in comparison to WT (post hoc Tukey test following Two-Way ANOVA, P<0.001). Bumetanide treatment for either 1 (1W) or 4 weeks (4W) rescued memory deficit in Ts65Dn mice (right, 1W: P<0.001 4W: P=0.001). All experimental groups showed negligible non-associative freezing when exposed to an untrained context (left). (C) Top, schematic representation of the object location test. Bottom, Ts65Dn mice showed strong spatial memory impairment, as compared to WT (post hoc Tukey test following Two-Way ANOVA, P<0.001). Bumetanide administration rescued spatial memory deficits both after 1 and 4 weeks of treatment (P<0.001). (D) Top, schematic representation of the novel object recognition task. Bottom, bumetanide treatment for either 1 or 4 weeks restored object novelty discrimination in Ts65Dn mice (post hoc Tukey test after Two-Way ANOVA, P<0.001). For all panels, histograms represent average±SEM, whereas circles indicate data from single animals.

The invention claimed is:

1. A method for reducing one or more symptoms associated with Down syndrome in a subject wherein said method comprises the administration of an effective amount of a modulator of a chloride transporter; wherein said modulator comprises bumetanide.

2. The method according to claim 1, wherein the effective amount ranges from about 0.01 mg to about 500 mg.

3. The method according to claim 1, wherein the modulator is administered directly to the subject in need thereof by subcutaneous, intramuscular, intravenous, intraocular, transdermal, topical, parenteral, intranasal and oral administration, or injection.

4. The method according to claim 1, wherein the subject is diagnosed with Down syndrome.

5. The method according to claim 1, wherein the subject is affected by Down syndrome.

6. The method according to claim 1, wherein said modulator is administered with at least one inhibitor of a transporter involved in the importation of chloride into neurons, wherein said inhibitor is selected from the group consisting of furosemide, ethacrynic acid, torsemide, azosemide, muzolimine, piretanide, tripamide, bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone.

* * * * *